(12) United States Patent
Shin et al.

(10) Patent No.: US 10,082,455 B2
(45) Date of Patent: Sep. 25, 2018

(54) APPARATUS AND METHOD FOR MICROPARTICLE SEPARATION BASED ON MICROFLUIDIC CHROMATOGRAPHY USING SURFACE ACOUSTIC WAVE

(71) Applicant: Korea University Research and Business Foundation, Seoul (KR)

(72) Inventors: Se Hyun Shin, Seoul (KR); Jeong Hoon Nam, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 318 days.

(21) Appl. No.: 14/758,249

(22) PCT Filed: Dec. 27, 2013

(86) PCT No.: PCT/KR2013/012279
§ 371 (c)(1),
(2) Date: Jun. 29, 2015

(87) PCT Pub. No.: WO2014/104798
PCT Pub. Date: Jul. 3, 2014

(65) Prior Publication Data
US 2015/0330887 A1    Nov. 19, 2015

(30) Foreign Application Priority Data

Dec. 28, 2012  (KR) .................. 10-2012-0155968

(51) Int. Cl.
*G01N 15/10*  (2006.01)
*B01D 15/38*  (2006.01)
(Continued)

(52) U.S. Cl.
CPC ......... *G01N 15/1056* (2013.01); *B01D 15/34* (2013.01); *B01D 15/3885* (2013.01);
(Continued)

(58) Field of Classification Search
CPC .... B01L 2200/0652; G01N 2015/1081; G01N 15/1056
See application file for complete search history.

(56) References Cited

U.S. PATENT DOCUMENTS 6,984,572 B2 *  1/2006  Nakatani ............. H01L 21/3043
                                                      257/E21.238
7,942,568 B1     5/2011  Branch et al.
(Continued)

FOREIGN PATENT DOCUMENTS

KR   10-2008-0052296   6/2008
KR       10-1183436    9/2012
(Continued)

OTHER PUBLICATIONS

International Preliminary Report on Patentability dated Jun. 30, 2015 From the International Bureau of WIPO Re. Application No. PCT/KR2013/012279 and Its Translation Into English.
(Continued)

*Primary Examiner* — John Fitzgerald

(57) ABSTRACT

The present invention related to an apparatus for separating micro-nano scale particles based on microfluidic chromatography using surface acoustic waves, comprising: a piezoelectric substrate; a pair of transducers, which are patterned on the piezoelectric substrate and generate surface acoustic waves when electric energy is applied to the piezoelectric substrate; a microfluidic chip, which is mounted on the piezoelectric substrate and include a microfluidic channel disposed between the pair of transducers, wherein a fluid including micro-nano scale particles flows in the microfluidic channel; and a detection unit, which detects micro-nano scale particles separated by the surface acoustic waves while the micro-nano scale particles pass through the microfluidic channel, wherein forces of the surface acoustic waves generated by the pair of transducers are formed in a direction (Continued)

opposite to a fluid flow to generate flow resistance to the micro-nano scale particles which flows in the microfluidic channel.

9 Claims, 4 Drawing Sheets

(51) Int. Cl.
*B01D 15/34* (2006.01)
*G01N 30/76* (2006.01)
*B01L 3/00* (2006.01)
*G01N 30/60* (2006.01)
*G01N 15/02* (2006.01)
*G01N 30/02* (2006.01)

(52) U.S. Cl.
CPC .......... *B01L 3/50273* (2013.01); *G01N 15/02* (2013.01); *G01N 30/6095* (2013.01); *G01N 30/76* (2013.01); *B01D 15/3866* (2013.01); *B01L 2200/0652* (2013.01); *B01L 2300/0816* (2013.01); *B01L 2300/0867* (2013.01); *B01L 2400/0436* (2013.01); *G01N 2015/1081* (2013.01); *G01N 2030/027* (2013.01)

(56) References Cited

U.S. PATENT DOCUMENTS

| | | | | |
|---|---|---|---|---|
| 8,266,951 B2* | 9/2012 | Kaduchak | ........ | G01N 15/1404 73/570.5 |
| 8,273,302 B2* | 9/2012 | Takahashi | ........... | B01D 21/283 204/157.42 |
| 8,573,060 B2* | 11/2013 | Huang | ............. | B01L 3/502761 73/570.5 |
| 8,790,916 B2* | 7/2014 | Achrol | ............. | B01L 3/502753 422/414 |
| 9,517,465 B2* | 12/2016 | Patel | ................ | B01L 3/502738 |
| 9,606,086 B2* | 3/2017 | Ding | ..................... | G01N 29/02 |
| 9,608,547 B2* | 3/2017 | Ding | ..................... | H02N 2/08 |
| 9,656,263 B2* | 5/2017 | Laurell | ............. | G01N 33/5005 |
| 9,670,477 B2* | 6/2017 | Lipkens | ................ | C12N 13/00 |
| 2004/0069717 A1* | 4/2004 | Laurell | ............... | A61M 1/3472 210/748.05 |
| 2007/0046142 A1* | 3/2007 | Obara | ..................... | H03H 3/08 310/313 R |
| 2007/0207548 A1* | 9/2007 | Blankenstein | ......... | B01D 57/02 436/63 |
| 2007/0231851 A1* | 10/2007 | Toner | ................ | B01L 3/502746 435/29 |
| 2007/0259424 A1* | 11/2007 | Toner | ................ | B01L 3/502746 435/372 |
| 2008/0181828 A1* | 7/2008 | Kluck | ..................... | A61M 1/36 422/128 |
| 2008/0245745 A1* | 10/2008 | Ward | ................... | G01N 1/4077 209/590 |
| 2009/0014360 A1* | 1/2009 | Toner | ................. | B01D 21/0087 209/208 |
| 2009/0061489 A1* | 3/2009 | Hanagata | ................ | B01L 7/525 435/91.2 |
| 2009/0087925 A1* | 4/2009 | Wagner | ................... | B01F 5/061 436/518 |
| 2009/0158823 A1* | 6/2009 | Kaduchak | .......... | G01N 15/1404 73/61.75 |
| 2009/0162887 A1* | 6/2009 | Kaduchak | .......... | G01N 15/1404 435/29 |
| 2009/0194420 A1* | 8/2009 | Mariella, Jr. | .......... | B01D 17/06 204/547 |
| 2009/0218223 A1* | 9/2009 | Manaresi | ............. | G01N 27/447 204/547 |
| 2009/0226994 A1* | 9/2009 | Lemor | .............. | B01L 3/502715 435/173.1 |
| 2010/0092339 A1* | 4/2010 | Takagi | .............. | B01L 3/502715 422/82.05 |
| 2010/0126922 A1* | 5/2010 | Takahashi | ............ | B01D 21/283 210/201 |
| 2010/0139377 A1 | 6/2010 | Huang et al. | | |
| 2010/0193407 A1* | 8/2010 | Steinberg | .......... | B01L 3/502761 209/155 |
| 2010/0304501 A1* | 12/2010 | Lee | ................... | B01L 3/502707 436/518 |
| 2011/0154890 A1* | 6/2011 | Holm | ................... | B01D 21/283 73/61.75 |
| 2012/0088295 A1* | 4/2012 | Yasuda | .................. | C12M 47/04 435/288.7 |
| 2012/0160746 A1* | 6/2012 | Thorslund | ......... | B01L 3/502761 209/552 |
| 2013/0043170 A1* | 2/2013 | Rose | .................... | B01D 21/283 209/659 |
| 2013/0192958 A1* | 8/2013 | Ding | .................... | B07C 5/3427 198/617 |
| 2014/0008307 A1* | 1/2014 | Guldiken | .......... | B01L 3/502761 210/748.05 |
| 2014/0033808 A1* | 2/2014 | Ding | ...................... | G01N 29/02 73/61.75 |
| 2015/0192546 A1* | 7/2015 | Weitz | ................... | G01N 29/222 137/13 |
| 2016/0016180 A1* | 1/2016 | Lopez | ................... | B01D 35/06 506/12 |

FOREIGN PATENT DOCUMENTS

| | | |
|---|---|---|
| WO | WO 02/072235 | 9/2002 |
| WO | WO 2014/104798 | 7/2014 |

OTHER PUBLICATIONS

International Search Report and the Written Opinion dated Apr. 24, 2014 From the Korean Intellectual Property Office Re. Application No. PCT/KR2013/012279 and Its Translation Into English.

Raeymaekers et al. "Manipulation of Diamond Nanoparticles Using Bulk Acoustic Waves", Journal of Applied Physics, AIP, 109: 014317-1-014317-8. 2011.

Tan et al. "Direct Visualization of Surface Acoustic Waves Along Substrates Using Smoke Particles", Applied Physics Letters, AIP, 91: 224101-1-224101-3, 2007.

* cited by examiner

APPARATUS AND METHOD FOR MICROPARTICLE SEPARATION BASED ON MICROFLUIDIC CHROMATOGRAPHY USING SURFACE ACOUSTIC WAVE

RELATED APPLICATIONS

This application is a National Phase of PCT Patent Application No. PCT/KR2013/012279 having International filing date of Dec. 27, 2013, which claims the benefit of priority of Korean Patent Application No. 10-2012-0155968 filed on Dec. 28, 2012. The contents of the above applications are all incorporated by reference as if fully set forth herein in their entirety.

TECHNICAL FIELD

The present invention relates to an apparatus and method for separating micro-nano scale particles based on microfluidic chromatography using surface acoustic waves, and more particularly, to an apparatus and method for separating micro-nano scale particles based on microfluidic chromatography using surface acoustic waves, by which micro-nano scale particles may be separated according to the characteristics of micro-nano scale particles by flow resistance formed by the surface acoustic waves.

BACKGROUND ART

In recent, according to change in the trend of research, there is increasing need of pre-treatment technique such as separation of micro-nano scale particles through microfluidic control of various sample fluids, etc. Particularly, as studies based on microfluidics are diversifying in addition to separation method such as the existing centrifuge requiring for expensive equipment, flow cytometry (FACS), or the like, techniques regarding separation of micro-nano scale particles in microfluidic chip have been actively developed.

Technique of separating micro/nano sized particles has been continuously studied for bioparticle separation for clinical research and biochemical analysis on platelets, circulating tumor cell (CTC), nucleated red blood cell (NRBC), platelet derived microparticle (PDMP) or the like, and nanoparticle separation for analysis of environmental impact of nanoparticles in environment such as air, water, soil, etc.

Among them, control technique of micro-nano scale particles using surface acoustic waves is technique having advantage in that no separate labeling is needed, and the technique is non-invasive and may be driven with low power. Prior research relating to the above-described technique is summarized as below.

U.S. Pat. No. 7,942,568 discloses a micromixer using surface acoustic waves in a microfluidic chip, and the micromixer has advantage in that the micromixer may be easily manufactured, easily combined to the microfluidic chip, and used with low power. The present invention has the same advantage of using surface acoustic waves in a microfluidic chip, but has difference in that the objective of the use of the apparatus is separating micro-nano scale particles.

US Patent Application Publication No. 2010/0139377 discloses an apparatus of focusing micro-nano scale particles using surface acoustic waves in a microfluidic chip, by which micro-nano scale particles may be focused at one or a plurality of pressure nodes formed in a microfluidic channel by surface acoustic waves.

Meanwhile, a thesis of 'Manipulation of diamond nanoparticles using bulk acoustic waves' (Journal of applied physics, 109, 014317, 2011) discloses a technique of patterning nanoparticles having a size of 5 nm included in a fluid in a circular or rectangular chamber at a pressure node point formed by surface acoustic waves. Here, patterning of nanoparticles is performed in the chamber, and thus the technique has disadvantage in that the patterning is not performed in continuous flow state of a microfluidic chip. Accordingly, in order to allow for continuous separation of nanoparticles in fluid flow, new type of device has to be developed.

Further, a thesis of 'Direct visualization of surface acoustic waves along substrates using smoke particles' (Applied physics letters, 91, 224101, 2007) discloses a technique of patterning and visualizing smoke particles (SP) having a size of 250 nm when surface acoustic waves are transmitted. Here, smoke particles are patterned for 15 to 30 seconds, the patterning is not performed in continuous flow state, and the technique relates to particles floating in the air. However, a technique of separating nano-scale particles with respect to particles floating in the fluid has never been developed.

SUMMARY OF THE INVENTION

The present invention is for addressing the above-described issue, and the objective of the present invention is directed to providing an apparatus and method for separating micro-nano scale particles based on microfluidic chromatography using surface acoustic waves, by which micro/nano sized particles may be separated according to particle size and characteristics in a continuous flow state in a microfluidic chip.

Technical Solution

In order to achieve the above-described objective, the present invention provides an apparatus for separating micro-nano scale particles based on microfluidic chromatography using surface acoustic waves, comprising: a piezoelectric substrate; a pair of transducers, which are patterned on the piezoelectric substrate and generate surface acoustic waves when electric energy is applied to the piezoelectric substrate; a microfluidic chip, which is mounted on the piezoelectric substrate and include a microfluidic channel disposed between the pair of transducers, wherein a fluid including micro-nano scale particles flows in the microfluidic channel; and a detection unit, which detects micro-nano scale particles separated by the surface acoustic waves while the micro-nano scale particles pass through the microfluidic channel, wherein forces of the surface acoustic waves generated by the pair of transducers are formed in a direction opposite to a fluid flow to generate flow resistance to the micro-nano scale particles which flows in the microfluidic channel.

The microfluidic channel may have at least one bending portion, and thus a flow direction and a direction of the surface acoustic wave may be adjusted.

The microfluidic channel may include a portion parallel to an extension line which connects the pair of transducers, and thus a plurality of pressure nodes may be formed in the flow direction. In this case, micro-nano scale particles flowing in the flow direction pass through the plurality of pressure nodes, and a force by which the micro-nano scale particles are held not to flow is applied at the pressure nodes. When the force is higher than a force by flow, the micro-nano scale particles may be captured at the pressure nodes.

The microfluidic channel may be provided with at least one fluid inlet. Further, the fluid inlet may include two or more inlets, and in this case, a sample fluid may be injected into at least one inlet, a sheath fluid may be injected into at least one of the other inlet, and a flux of each fluid may be independently controlled, and thus a position of the sample fluid may be hydraulically adjusted.

According to an embodiment of the present invention, the position of the sample fluid may be hydraulically adjusted by forming three inlets at the inlet portion of the microfluidic channel. For example, when the sample fluid is injected into a lower inlet, and the sheath fluid is supplied at a high flux through center and upper inlets, the sample fluid may flow along a lower wall of the microfluidic channel. As described above, a speed of the sample fluid flowing along a wall surface is maintained at a relatively low speed due to a friction force of the wall surface, and may be easily controlled by a force applied in the outside, that is, a force generated by surface acoustic waves.

The microfluidic channel may have a zigzag shape or a winding shape. The piezoelectric substrate may be formed of a lithium niobate ($LiNbO_3$) or quartz material.

The pair of transducers may be formed by patterning gold on a chrome layer which is an adhesive layer formed on a surface of the piezoelectric substrate and may be interdigitated.

The microfluidic channel may be attachably and detachably mounted on the piezoelectric substrate.

An end portion of the microfluidic channel may be provided with a fluid outlet.

Surface acoustic waves generated by the pair of transducers may meet each other to form standing surface acoustic waves, and thus a plurality of pressure nodes may be periodically formed in a flow direction of the fluid.

Further, the pair of transducers may independently work, and may form one surface acoustic wave acting in a direction opposite to the flow direction, and thus the surface acoustic wave may act as a force for pushing particles inside the fluid to an opposite direction.

The detection unit may be installed before the fluid outlet in the flow direction of the fluid.

The detection unit may include an electrical impedance sensor or a photospectrometer.

Further, the present invention provides a method for separating micro-nano scale particles based on microfluidic chromatography using surface acoustic waves, comprising: bonding a microfluidic chip on a piezoelectric substrate patterned with a pair of transducers; injecting a fluid which includes micro-nano scale particles through a fluid inlet of the microfluidic chip; generating surface acoustic waves by applying electric energy having a specific operating frequency to the pair of transducers; forming a pressure node in a microfluidic channel of the microfluidic chip by standing surface acoustic waves formed when the surface acoustic waves generated from each of the pair of transducers meet each other, such that the pressure node acts as flow resistance; and detecting micro-nano scale particles separated while passing through the microfluidic channel.

Advantageous Effects

According to the embodiment of the present invention, although particles are small particles having a nano scale, the particles are subject to flow disturbing interference by surface acoustic waves over a plurality of times, causing a difference in a flow speed, and thus the particles can be separated according to a particle size in a continuous flow state, and since the particles can be detected after separation, micro and nano sized materials can be separated and fractionated only by injecting a sample.

Further, since a part to which a blood sample contacts can be manufactured as a disposable microfluidic chip, a separate complicated cleaning process is not required, and the apparatus and method according to the embodiment of the present invention can be easily used at a site such as a clinical laboratory, a laboratory, etc.

DESCRIPTION OF SPECIFIC EMBODIMENTS OF THE INVENTION

Hereinafter, an apparatus for separating micro-nano scale particles based on microfluidic chromatography according to an embodiment of the present invention will be described in detail with reference to the appended drawings.

Figure 1:
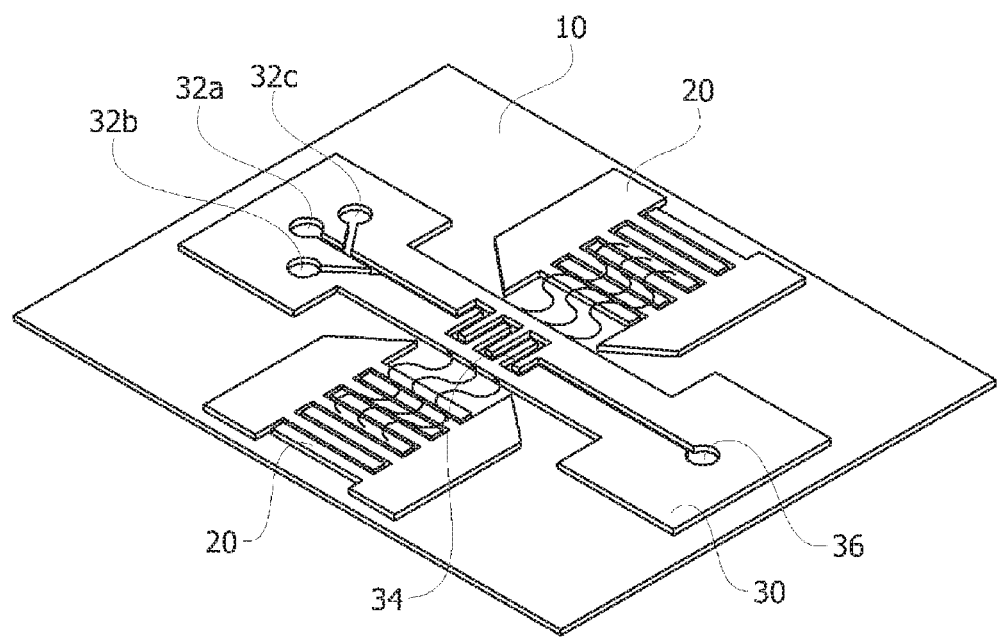
FIG. 1 is a perspective view illustrating an apparatus for separating micro-nano scale particles based on microfluidic chromatography according to an embodiment of the present invention.

FIG. 1 is a perspective view illustrating an apparatus for separating micro-nano scale particles based on microfluidic chromatography according to an embodiment of the present invention.

As illustrated in the drawing, the apparatus for separating micro-nano scale particles based on microfluidic chromatography according to the embodiment of the present invention may largely include a piezoelectric substrate 10, at least one transducer 20 and a microfluidic chip 30.

First, the piezoelectric substrate 10 may convert electric energy to mechanical energy such as oscillation when applied with electric energy, and a substrate formed of lithium niobate ($LiNbO_3$) or quartz which is a representative piezoelectric material may be used as the piezoelectric substrate.

The microfluidic chip 30 will be described with reference to FIG. 1. The microfluidic chip 30 may largely include a fluid inlet 32, a curved-tube type microfluidic channel 34 having a zigzag shape and a fluid outlet 36. Further, the microfluidic chip 30 may be attachably and detachably mounted on the piezoelectric substrate 10.

The microfluidic channel 34 may have a cross section in the shape of a polygon such as a quadrangle, a circle or an ellipse. For example, when a cross section of the microfluidic channel is quadrangular, the length of an edge may range from 1 to 1,000 μm, preferably 10 to 200 μm, and more preferably 20 to 50 μm. When a cross section of the microfluidic channel is circular, the diameter of the circular channel may also be in the above-described range.

At least one fluid inlet 32 may be formed at an inlet portion of the microfluidic channel 34, and for example, may include two or more fluid inlets. Three fluid inlets 32a, 32b and 32c are exemplified in FIG. 1. That is, as illustrated in the drawing, the fluid inlet may be divided into an upper fluid inlet 32a, a lower fluid inlet 32b and a center fluid inlet 32c. However, the number of the fluid inlet may be suitably modified according to the need.

As the fluid inlets 32a, 32b and 32c are formed as a plurality, the microfluidic channel 34 may be also separated into several branches at the inlet portion. The microfluidic channel 34 may be branched at several points as illustrated in the drawing, or may be branched at one point.

As illustrated in FIG. 1, the upper fluid inlet 32a may be connected to a central microfluidic channel 34, a branching portion of the microfluidic channel 34 connected to the lower fluid inlet 32b may join the central microfluidic channel 34 at a downstream side, and a branching portion of the microfluidic channel 34 connected to the center fluid inlet 32c may join the central microfluidic channel 34 at a intermediate point between a starting point and a junction at a downstream side. A branching position of the microfluidic channel 34 may be suitably modified according to the need.

A sample fluid may be injected into at least one inlet, a sheath fluid may be injected into at least one of the other inlet, and a flux of each fluid may be independently controlled, and thus a position of the sample fluid may be hydraulically adjusted. Here, the sheath fluid may refer to a carrier fluid carrying a sample fluid.

For example, when the sample fluid is supplied at a downstream side of the microfluidic channel 34 though the lower fluid inlet 32b, and the sheath fluid is supplied at a high flux through the upper fluid inlet 32a and the center fluid inlet 32c, the sample fluid may flow along a lower wall of the microfluidic channel 34. As described above, a speed of the sample fluid flowing along a wall surface is maintained at a relatively low speed due to a friction force of the wall surface, and may be easily controlled by a force applied in the outside, that is, a force generated by surface acoustic waves.

The microfluidic channel 34 of the microfluidic chip 30 may include a straight channel section shortly before the fluid outlet 36 so as to access a detection unit 40 for detecting micro-nano scale particles, which flow toward the fluid outlet 36 after being separated according to the characteristics, according to the time shortly before the fluid outlet 36.

When electric energy is applied to the piezoelectric substrate 10 by the transducers 20 arranged at the right and left sides of the microfluidic channel 34, oscillation with a constant frequency is generated on a surface of the piezoelectric substrate 10 according to inherent signal values applied from the transducers 20, and according to the gap and size of the transducers 20, and the oscillation is referred to as surface acoustic wave (SAW). Here, the microfluidic channel 34 is interposed between the two transducers 20, and when two surface acoustic waves meet, standing surface acoustic wave (SSAW) is generated. That is, a node at which the waves dissipate due to the overlapping and offsetting of the waves, or an unstable node at which the waves are amplified, may be formed. The former node is referred to as a pressure node, while the latter node is referred to as an anti-pressure node.

In general, particles which are present in a fluid come into the pressure node formed by overlapped surface acoustic waves, and particles may be separated using this phenomenon. Since a force of the surface acoustic wave pushing the particles toward the pressure node is proportional to a particle size, that is, to a particle volume, and thus the speed of the particles moving toward the pressure node may be proportional to the cube of a particle diameter, that is, the speed of the particles having a large diameter may be the cube of the speed of the particles having a small diameter. A technique for separating particles according to the particle size in a continuous flow state using the above-described characteristics has been disclosed (Nam et al., Lab on a Chip 2011).

In a conventional method, a method and apparatus, in which the arrangement of the pressure nodes is parallel to a flow direction, particles are flown in a main flow direction while the particles are pushed in a transverse direction by surface acoustic waves to change a flow line of each particle, and thereby the particles are moved to different chambers from each other at a fluid outlet, have been invented. The above-described method has advantage in that the particles are continuously and simultaneously separated to the different chambers from each other. Particularly, the particles may be separated according to the size without any special label in the particles.

However, although the above-described separation method has excellent characteristics, the separation method is only applicable to micro-scale particles, and nano-scale particles may not be separated practically because the separation of nano-scale particles only using the force of the surface acoustic wave takes a lot of time. Here, the size of the micro-scale particles may refer to, for example, 0.1 μm or more, preferably 0.5 μm or more, more preferably 1 μm or more, and the size of the nano-scale particles may refer to, for example, less than 1,000 nm, preferably less than 500 nm, and more preferably less than 100 nm.

In order to overcome the above-described limitation of existing technique for separating micro-nano scale particles based on surface acoustic waves, in the present invention a technique for separating nano-scale particles by combining the surface acoustic wave technique with the chromatography technique is developed. Further details of the technique will be described with reference to FIGS. 2 and 3.

After the sample fluid in which various particles are mixed is injected into the fluid inlets 32, the sample fluid starts to flow by a precision pump. Here, a channel may be configured such that a flow along the microfluidic channel 34 passes through a line of gathered pressure nodes perpendicularly or at a constant angle, and a plurality of pressure node lines are arranged in the flow direction.

For example, the microfluidic channel 34 may include at least one bending portion. That is, the microfluidic channel 34 may have a plurality of bending portions such that the flow direction is bent perpendicularly, and the microfluidic channel 34 preferably includes a portion parallel to an extension line which connects the pair of the transducers 20 such that the surface acoustic waves are formed in a direction opposite to the flow direction.

Further, the microfluidic channel 34 may have a zigzag shape or a winding shape, and thereby a plurality of pressure nodes may be formed with respect to the flow direction.

Here, the shape of the microfluidic channel 34 exemplified as above is merely for an example, and any shape may be applicable insofar as the shape allows the surface acoustic waves to be formed in the direction opposite to the flow direction.

When the particles move in the fluid flow and pass through pressure node lines, the particles are applied with the force by the surface acoustic waves to hold or stop the particles at pressure nodes. Since the above-described force is proportional to the particle size, a force applied to nanoparticles is too low, and thus there is a limitation to stop the particles, but fine-scale flow resistance may be generated at least.

Accordingly, when the particles pass through the microfluidic channel 34 in which a plurality of pressure node lines are arranged, total accumulated flow resistance which one particle experiences grows to be considerable amount or very remarkable amount while the particle passes through all sections of the microfluidic channel 34. The value of the above-described flow resistance differ according to the particle size, consequently large particles experience high flow resistance, thus a time at which the large particles reach the fluid outlet 36 is delayed, and a time at which small particles reach the fluid outlet 36 is relatively shortened.

Figure 4:
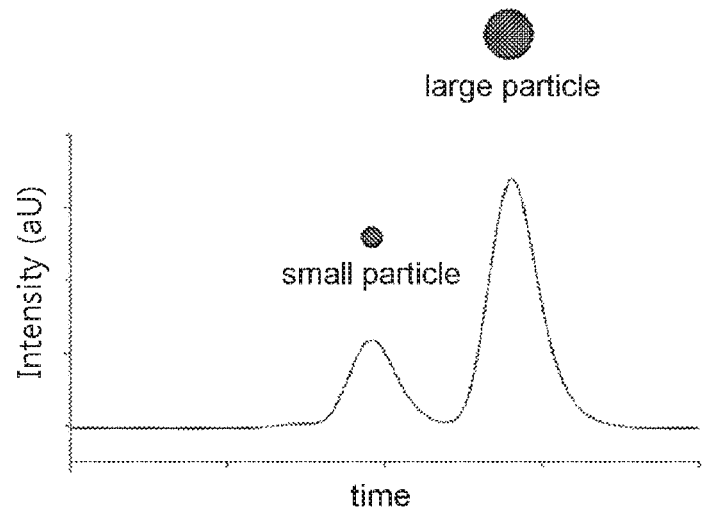
FIG. 4 is a graph of a signal optically detected when particles separated according to an embodiment of the present invention pass through a detection unit by a time gap.

As described above, a time in which the sample fluid reach the fluid outlet 36 after being injected to the fluid inlet 32 refers to a retention time, and the sample fluid may be separated through a difference in the retention time according to the particle size. When the particles separated as described above pass through the detection unit 40 installed before the fluid outlet 36, optical characteristic curves according to the particle size may be obtained using a light source 42 and a photospectrometer 44, and thereby the size or shape of the particles may be classified. Such an optical characteristic curve is shown in FIG. 4.

Figure 5:
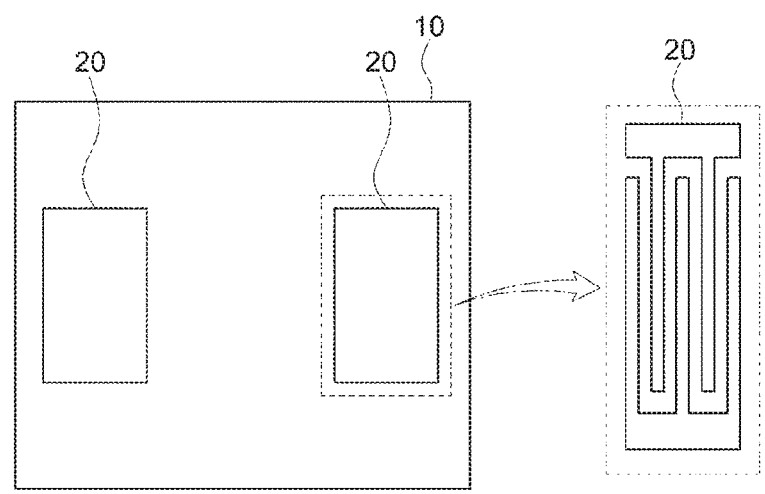
FIG. 5 is a block diagram of an interdigital transducer formed according to an embodiment of the present invention.

The transducers 20 will be described with reference to FIG. 5. FIG. 5 is a plan view of interdigital transducers 20 (IDTs) patterned on the piezoelectric substrate 10 of the apparatus for separating micro-nano scale particles according to an embodiment of the present invention.

Referring to the drawing, the interdigital transducers 20 are interdigitated from a lateral view, and may be manufactured by forming a chrome layer which is an adhesive layer on the surface of the piezoelectric substrate 10, and patterning gold on the chrome layer. The transducers 20 are required to be designed to have dimensions (such as a width or the like) suitable to the characteristics of the micro-nano scale particles to be separated, and accordingly, a specific operating frequency of electric energy applied to the transducers 20 may be determined.

An accurate operating frequency of electric energy applied to the transducers 20 may be an operating frequency applied when a fixed input power and an AC signal having a variable frequency are applied to any one of the transducers 20, and the opposite transducer 20 which acts as a receiver has a maximum output signal.

Figure 2:
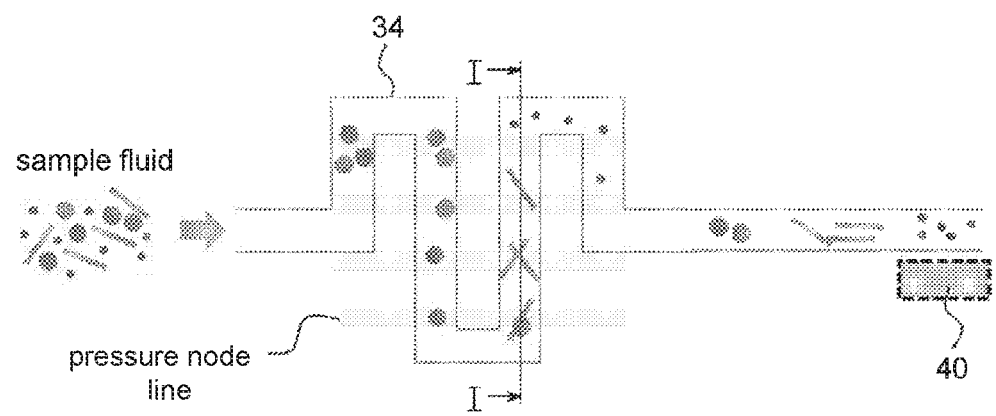
FIG. 2 is an exemplary view illustrating a plurality of pressure nodes formed in a microfluidic channel according to an embodiment of the present invention and particles being separated according to a particle size due to the pressure nodes.
Figure 3:
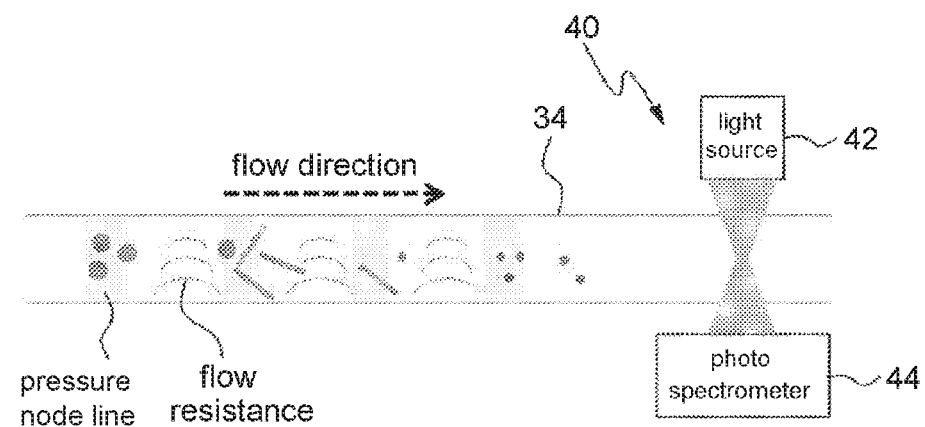
FIG. 3 is a cross-sectional view taken along line I-I in FIG. 2.

When electric energy having a specific operating frequency is applied to the transducers 20, electric energy is converted to mechanical energy by the piezoelectric substrate 10 to generate surface acoustic waves, and when the pair of transducers 20 are positioned at both sides as shown in FIG. 2, standing surface acoustic waves may be generated.

When the surface acoustic waves are used, nano-materials having a high aspect ratio such as nanowires are aligned in an electrode direction. That is, the direction of the nanowires which has been aligned and flown in the flow direction is changed to an electrode direction at a site in which the surface acoustic waves are applied, causing the nanowires to stop. The surface acoustic waves may be used to align the nanowires in a predetermined direction using the above-described phenomenon.

Further, the piezoelectric substrate 10 providing surface acoustic waves and the microfluidic chip 30 are attachably and detachably formed in the embodiment of the present invention, and thus they may be attached to each other only upon the use and the microfluidic chip 30 may be discarded as a disposable chip after the use.

Further, the surface acoustic waves may be substituted with bulk acoustic waves. That is, the surface acoustic waves may be transmitted from a lateral side of the channel instead of being generated and transmitted from a bottom surface of a fluidic channel by forming the channel inside the piezoelectric substrate 10.

Hereinafter, a method for separating micro-nano scale particles using the above-described apparatus for separating micro-nano scale particles based on microfluidic chromatography according to an embodiment of the present invention will be described in detail with reference to the appended drawings.

Figure 6:
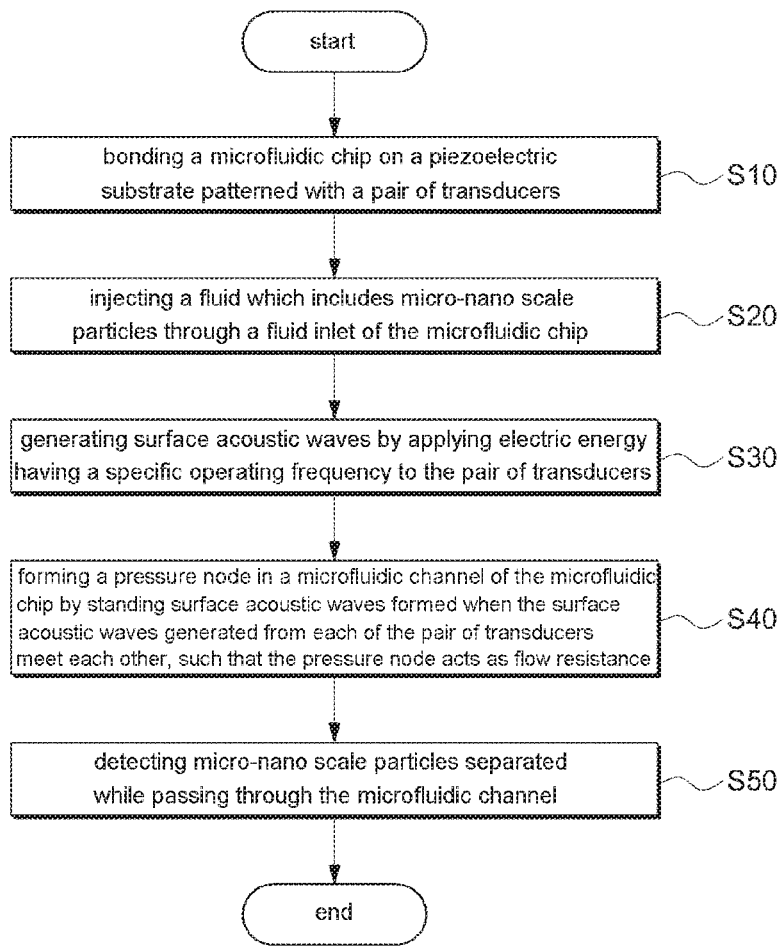
FIG. 6 is a flowchart illustrating a method for separating micro-nano scale particles based on microfluidic chromatography according to an embodiment of the present invention.

FIG. 6 is a flowchart illustrating a method for separating micro-nano scale particles based on microfluidic chromatography according to an embodiment of the present invention.

As illustrated in the drawing, the transducers 20 patterned on the piezoelectric substrate 10 and the disposable microfluidic chip 30 may be manufactured using soft lithography. Here, the microfluidic chip 30 is bonded to the piezoelectric substrate 10 patterned with the transducers 20 (S10).

Next, a fluid including micro-nano scale particles is injected into the fluid inlet 32 of the microfluidic chip 30 using a syringe pump (S20).

Meanwhile, the pair of transducers 20 patterned with gold on the surface of the piezoelectric substrate 10 are interdigitated transducers (IDTs) which are in the interdigitated form, and when electric energy having a specific operating frequency is applied thereto, surface acoustic waves are generated from each transducer 20 (S30).

The generated surface acoustic waves meet at an intermediate point between the pair of transducers 20, and form standing surface acoustic waves through overlapping and offsetting. The intermediate point between the pair of transducers 20 is coated with a film for the continuous use of the piezoelectric substrate 10, and the disposable microfluidic chip 30 is bonded to an upper part of the film. The microfluidic channel 34 positioned at a center point is in the form of a continuous bent tube, and pressure nodes derived from standing surface acoustic waves generated by the pair of transducers 20 are repeatedly formed along the flow direction, and thereby acts as flow resistance in the flow (S40).

The degree in which the particles included in the fluid flowing in the microfluidic channel 34 are concentrated and gathered at the pressure nodes differs according to the size, deformability, density or the like of the particles, and accordingly, the micro-nano scale particles may be separated according to the characteristics. More specifically, since more amount of relatively large micro-nano scale particles are gathered at the pressure nodes as compared to the amount of small micro-nano scale particles, the relatively large micro-nano scale particles consume the relatively long time as compared to the small micro-nano scale particles at the pressure nodes in which the micro-nano scale particles meet while flowing along the fluid flow.

A time at which the micro-nano scale particles pass through the microfluidic channel 34 differs according to the characteristics of the micro-nano scale particles, and thus the micro-nano scale particles may be separated according to the difference in the time at which the micro-nano scale particles flow toward the fluid outlet 36. As the detection unit 40 for detecting the micro-nano scale particles flowing toward the fluid outlet 36 after being separated according to the characteristics of the micro-nano scale particles, the light source 42, the photospectrometer 44, and the like may be used to detect a signal according to the time (S50).

The scope of the present invention is not limited to the above-described embodiments and is defined as described in claims, and it is clear that those skilled in the art to which this invention belongs may amend and modify the embodiment, not deviating from the scope of the essential features of the claims.

DESCRIPTION OF REFERENCE NUMERALS

10: piezoelectric substrate
20: transducer
30: microfluidic chip
32: fluid inlet
34: microfluidic channel
36: fluid outlet
40: detection unit
42: light source
44: photo spectrometer

What is claimed is:

1. An apparatus for separating nano scale particles based on microfluidic chromatography using surface acoustic waves, comprising:
   a piezoelectric substrate;
   a pair of transducers, which are patterned on the piezoelectric substrate and generate surface acoustic waves when electric energy is applied to the piezoelectric substrate;
   a microfluidic chip, which is mounted on the piezoelectric substrate and include a microfluidic channel disposed between the pair of transducers, wherein a fluid including nano scale particles flows in the microfluidic channel; and
   a detection unit, which detects nano scale particles separated by the surface acoustic waves while the nano scale particles pass through the microfluidic channel,
   wherein forces of the surface acoustic waves generated by the pair of transducers are formed in a direction opposite to a fluid flow to generate flow resistance to the nano scale particles which flows in the microfluidic channel;
   wherein the microfluidic channel has at least one bending portion;
   wherein surface acoustic waves generated by the pair of transducers meet each other to form standing surface acoustic waves, and thus a plurality of pressure nodes are periodically formed in a flow direction of the fluid;
   wherein an end portion of the microfluidic channel is provided with a fluid outlet;
   wherein the detection unit is installed before the fluid outlet in a flow direction of the fluid;
   wherein the microfluidic channel is configured such that a flow along the microfluidic channel perpendicularly passes through a plurality of pressure node lines which are arranged in the flow direction.

2. The apparatus of claim 1, wherein the microfluidic channel has a zigzag shape or a winding shape.

3. The apparatus of claim 1, wherein the piezoelectric substrate is formed of a lithium niobate (LiNbO$_3$) or quartz material.

4. The apparatus of claim 1, wherein the pair of transducers are in an interdigitated form and are formed by patterning gold on a chrome layer which is an adhesive layer formed on a surface of the piezoelectric substrate.

5. The apparatus of claim 1, wherein the microfuidic chip is attachable and detachably mounted on the piezoelectric substrate.

6. The apparatus of claim 1, wherein the detection unit includes an electrical impedance sensor or a photospectrometer.

7. The apparatus of claim 1, wherein the microfluidic channel is provided with at least one fluid inlet.

8. The apparatus of claim 7, wherein the fluid inlet includes two or more inlets, a sample fluid is injected into at least one inlet, a sheath fluid is injected into at least one of the other inlet, and a flux of each fluid is independently controlled, and thus a position of the sample fluid is hydraulically adjusted.

9. A method for separating nano scale particles based on microfluidic chromatography using surface acoustic waves, comprising:
   bonding a microfluidic chip on a piezoelectric substrate patterned with a pair of transducers;
   injecting a fluid which includes nano scale particles through a fluid inlet of the microfluidic chip;
   generating surface acoustic waves by applying electric energy having a specific operating frequency to the pair of transducers;
   forming a pressure node in a microfluidic channel of the microfluidic chip by standing surface acoustic waves formed when the surface acoustic waves generated from each of the pair of transducers meet each other, such that the pressure node acts as flow resistance; and
   detecting nano scale particles separated while passing through the microfluidic channel;
   wherein the microfluidic channel has at least one bending portion;
   wherein surface acoustic waves generated by the pair of transducers meet each other to form standing surface acoustic waves, and thus a plurality of pressure nodes are periodically formed in a flow direction of the fluid;
   wherein an end portion of the microfluidic channel is provided with a fluid outlet;
   wherein the detection unit is installed before the fluid outlet in a flow direction of the fluid;
   wherein the microfluidic channel is configured such that a flow along the microfluidic channel perpendicularly passes through a plurality of pressure node lines which are arranged in the flow direction;
   wherein the pressure node lines are the same as the line of gathered pressure nodes.

* * * * *